United States Patent [19]

Blade et al.

[11] Patent Number: 5,352,822

[45] Date of Patent: Oct. 4, 1994

[54] PESTICIDES

[75] Inventors: Robert J. Blade; George S. Cockerill; John E. Robinson, all of Hertfordshire, England

[73] Assignee: Roussel Uclaf, France

[21] Appl. No.: 43,817

[22] Filed: Apr. 7, 1993

Related U.S. Application Data

[60] Division of Ser. No. 835,683, Feb. 14, 1992, Pat. No. 5,229,424, which is a continuation-in-part of Ser. No. 729,847, Jul. 12, 1991, Pat. No. 5,202,356, which is a continuation of Ser. No. 436,803, Nov. 15, 1989, abandoned.

Foreign Application Priority Data

Nov. 16, 1988 [GB] United Kingdom ............. 8826760.4

[51] Int. Cl.[5] .............................................. C07C 63/33
[52] U.S. Cl. ................................... 562/492; 546/339; 546/340; 546/342; 546/346; 549/29; 549/78; 549/79; 556/436; 556/442; 556/465; 558/178; 558/205; 558/206; 558/215; 558/217; 560/100; 560/102; 560/124; 562/506; 562/867; 568/14; 568/16; 568/17; 568/303; 568/329; 568/420; 568/425
[58] Field of Search .............. 562/492, 506, 867; 560/102, 124; 558/178, 217, 205, 206, 215; 568/14, 17, 329, 425, 16, 303, 420; 546/339, 340, 341, 346; 556/436, 442, 465

[56] References Cited

PUBLICATIONS

Le Stanc et al., *Can. J. Chem.*, vol. 63, No. 11, pp. 2958–2960 (1985).
Itoh et al., *J. Chem. Soc. Chem. Comm.*, 1979 (3), pp. 101–102.
De Puy et al., *J. Org. Chem.*, vol. 29, No. 10, pp. 2813–2815 (1964).

*Primary Examiner*—Richard L. Raymond
*Assistant Examiner*—Scott C. Rand
*Attorney, Agent, or Firm*—Nixon & Vanderhye

[57] ABSTRACT

The present invention discloses pesticidally active compounds of formula (II)

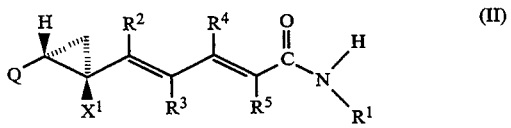

or a salt thereof, wherein Q is an monocyclic aromatic ring, or fused bicyclic ring system of which at least one ring is aromatic containing 9 or 10 atoms of which one may be nitrogen and the rest carbon each ring system being optionally substituted, or Q is a dihalovinyl group or a group $R^6$—C≡C— where $R^6$ is $C_{1-4}$ alkyl, tri $C_{1-4}$ alkylsilyl, halogen or hydrogen; $R^2$, $R^3$, $R^4$ and $R^5$ are the same or different with at least one being hydrogen and the others being independently selected from hydrogen, halo, $C_{1-4}$ alkyl or $C_{1-4}$ haloalkyl; and $R^1$ is selected from hydrogen and $C_{1-8}$ hydrocarbyl optionally substituted by dioxalanyl, halo, cyano, trifluoromethyl, trifluoromethylthio or $C_{1-6}$ alkoxy and $X^1$ is hydrogen, fluoro or chloro.

1 Claim, No Drawings

PESTICIDES

This is a division of application Ser. No. 07/835,683, filed Feb. 14, 1992, now U.S. Pat. No. 5,229,424; which in turn is a continuation in part of Ser. No. 07/729,847, filed Jul. 12, 1991, now U.S. Pat. No. 5,202,356; which is a FWC of Ser. No. 07/436,803, filed Nov. 15, 1989, abandoned.

This invention relates to pesticidal compounds, processes for their preparation, compositions containing them and to their use in the treatment of pests.

Unsaturated amides having a methylene chain of 1 to at least 10 carbon atoms optionally including at least one oxygen or additional methylene group are known as pesticides or insecticides having various terminating groups which include within their scope optionally substituted phenyl (European Application Nos. 228222, 194764, 225011, Japanese Application No 57-212150, Meisters and Wailes: Aust. J. Chem. 1966, 19, 1215, Vig et al: J. Ind. Chem. Soc. 1974, 51(9), 817) or pyridyl (European Application 269457) or fused bicyclic ring system (European Application Nos. 143593, 228853), dihalovinyl or optionally substituted ethynyl (European Application 228222).

No disclosure is made of any cycloalkyl interstitial group linking the diene unit to the terminating group.

H. O. Huisman et al, Rev. trav. chim. 77, 97–102, (1958) discloses a group of 5-(2,6,6-trimethyl cyclohexenyl)2,4-pentadienamides as insecticides.

European Patent Application 369762A (U.S. patent application Ser. No. 07/436803) provides a compound of formula (I):

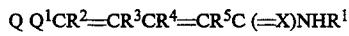

Q Q$^1$CR$^2$=CR$^3$CR$^4$=CR$^5$C (=X)NHR$^1$ or a salt thereof, wherein Q is an monocyclic aromatic ring, or fused bicyclic ring system of which at least one ring is aromatic containing 9 or 10 atoms of which one may be nitrogen and the rest carbon each ring system being optionally substituted, or Q is a dihalovinyl group or a group R$^6$—C≡C— where R$^6$ is C$_{1-4}$ alkyl, tri C$_{1-4}$ alkylsilyl, halogen or hydrogen; Q$^1$ is a 1,2-cyclopropyl ring optionally substituted by one or more groups selected from C$_{1-3}$ alkyl, halo, C$_{1-3}$ haloalkyl, alkynyl, or cyano; R$^2$,R$^3$, R$^4$ and R$^5$ are the same or different with at least one being hydrogen and the others being independently selected from hydrogen, halo, C$_{1-4}$ alkyl or C$_{1-4}$ haloalkyl; X is oxygen or sulphur; and R$^1$ is selected from hydrogen and C$_{1-8}$ hydrocarbyl optionally substituted by dioxalanyl, halo, cyano, trifluoromethyl, trifluoromethylthio or C$_{1-6}$ alkoxy.

It has now been discovered that certain enantiomers of the compounds of the formula (I) have a surprisingly high level of insecticidal activity compared to the other isomers.

Accordingly, the present invention provides a compound of the formula (II):

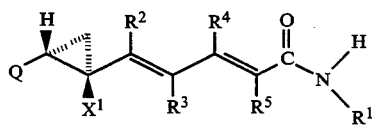

wherein Q and R$^1$ to R$^5$ are as hereinbefore defined and X$^1$ is hydrogen, fluoro or chloro.

When Q is a monocyclic aromatic ring, this is suitably phenyl, pyridyl or thienyl and preferably phenyl. When Q is a bicyclic ring system, this is preferably naphthyl.

When Q contains an aromatic system, suitable substituents include one to four groups selected from C$_{1-6}$ hydrocarbyl, C$_{1-6}$ alkoxy or methylenedioxy, each optionally substituted by one to three halos, or from halo, cyano or nitro, or the substituent is a group S(O)$_n$R$^7$ wherein n is 0, 1 or 2 and R$^7$ is C$_{1-6}$ alkyl optionally substituted by one or more halos or R$^7$ is amino optionally substituted by one or two C$_{1-6}$ alkyl groups or the substituent is a group NR$^8$R$^9$ where R$^8$ and R$^9$ are independently selected from hydrogen, C$_{1-6}$ alkyl or a group COR$^{10}$ where R$^{10}$ is C$_{1-6}$ alkyl.

The Q ring system normally contains up to three substituents and is suitably unsubstituted or substituted by one, two or three substituents such as halo or C$_{1-4}$ haloalkyl such as trifluoromethyl. The substitution of the Q ring system depends upon the nature of this ring system but is preferably at the 3, 4 or 5 positions when Q is a 6-membered ring.

Suitably R$^2$, R$^3$, R$^4$ and R$^5$ are chosen from hydrogen, methyl or fluoro. Suitably the stereochemistry of the double bonds is (E). Suitably when R$^3$ or R$^5$ is fluoro then the stereochemistry of the double bond to which R$^3$ R$^5$ or is attached is (Z). Preferably R$^2$ is hydrogen, R$^3$ is hydrogen or fluoro, R$^5$ is hydrogen or fluoro and R$^4$ is hydrogen or C$_{1-4}$ alkyl, most preferably methyl.

Suitably R$^1$ is alkyl optionally substituted by cycloalkyl, dioxalanyl, or R$^1$ is C$_{2-5}$ alkenyl. Most suitably R$^1$ is a branched chain C$_{4-6}$ alkyl group, such as isobutyl, 1,2-dimethylpropyl, 1,1,2-trimethyl propyl, 2,2-dimethylpropyl or R$^1$ is 2-methylprop-2-enyl or (2-methyl-1,3-dioxalan-2-yl) methyl. Preferably R$^1$ is isobutyl or 2-methyl-prop-2-enyl where R$^2$ and R$^3$ are hydrogen, R$^4$ is methyl and R$^5$ is hydrogen or methyl.

Preferably the stereo metric configuration of the cyclopropyl group in the chain is such that the group Q and the carbon side chain are attached to the ring to give trans geometry.

When X$^1$ is fluoro or chloro, the absolute configuration about the cyclopropane ring is preferably (1R,2S). When X$^1$ is hydrogen, the absolute configuration about the cyclopropane ring is preferably (1S,2R).

One suitable group of compounds of the formula (II) is that of the formula (III):

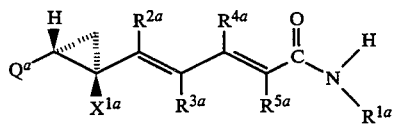

or a salt thereof, wherein Q$^a$ is a substituted phenyl or pyridyl group; X$^{1a}$ is hydrogen, fluoro or chloro; R$^{2a}$,R$^{3a}$,R$^{4a}$ and R$^{5a}$ are the same or different with at least one being hydrogen and the others being independently selected from hydrogen, halo, C$_{1-4}$ alkyl or C$_{1-4}$ haloalkyl and R$^{1a}$ is selected from hydrogen and C$_{1-6}$ hydrocarbyl optionally substituted by dioxalanyl, halo, cyano, trifluoromethyl, trifluoromethylthio or C$_{1-6}$ alkoxy.

Suitable substituents for Q$^a$ include one or more groups selected from halo, cyano, nitro, C$_{1-6}$ alkyl, C$_{1-6}$ alkoxy and methylenedioxy, each optionally substituted by one to five halos or the substituent is a group S(O)$_n$-R$^{7a}$ wherein n is 0, 1 or 2 and R$^{7a}$ is C$_{1-6}$ alkyl optionally substituted by halo or R$^{7a}$ is amino.

Suitably $R^{2a}$, $R^{3a}$, $R^{4a}$ and $R^{5a}$ are chosen from hydrogen, methyl, or fluoro.

Suitably $R^{1a}$ is $C_{1-6}$ alkyl optionally substituted by dioxalanyl, or $R^{1a}$ is $C_{2-5}$ alkenyl. Most suitably $R^{1a}$ is a branched chain $C_{4-6}$ alkyl group, such as isobutyl, 1,2-dimethylpropyl, 1,1,2-trimethyl propyl, 2,2-dimethylpropyl or $R^{1a}$ is 2-methyl-prop-2-enyl or (2-methyl-1,3-dioxalan-2-yl) methyl. Preferably $R^{1a}$ is isobutyl or 2-methylprop-2-enyl where $R^{2a}$ and $R^{3a}$ are hydrogen and $R^{4a}$ is methyl.

One preferred group of compounds of the formula (III) includes those wherein $R^{2a}$, $R^{3a}$ and $R^{5a}$ are each hydrogen.

A further preferred group of compounds of the present invention includes those of formula (II) wherein $R^2$ is hydrogen.

Preferred compounds include those wherein Q is substituted phenyl, $R^4$ is methyl or hydrogen, $R^2$ is hydrogen, $R^3$ and $R^5$ are hydrogen or fluoro and $R^1$ is isobutyl or 1,2-dimethylpropyl or 2-methylprop-2-enyl and X is oxygen or sulphur.

Thus, preferred compounds of the formula (II) include
(c refers to the substituent cis, relative (r) to another substituent)
(−)-(2E,4E)-N-(2-Methylprop-2-enyl)-5-[(1R,2S)-c-2-(3,4-dibromophenyl)-r-1-fluorocyclopropyl]-3-methylpenta-2,4-dienamide
(−)-(2E/Z,4E)-N-(2-Methylprop-2-enyl)-5-[1R,2S)-c-2-(3,4-dibromophenyl)-r-1-fluorocyclopropyl]-3-methylpenta-2,4-dienamide
(+)-(2E,4E)-N-(2-Methylprop-2-enyl)-5-[(1S,2R)-c-2-(3,4-dibromophenyl)-r-1-fluorocyclopropyl]-3-methylpenta-2,4-dienamide
(+)-(2E/Z,4E)-N-(2-Methylprop-2-enyl)-5-[(1S,2R)-c-2-(3,4-dibromophenyl)-r-1-fluorocyclopropyl]-3-methylpenta-2,4-dienamide
(+)-(2E,4E)-N-Isobutyl-5-[(1S,2R)-c-(3,4-dichlorophenyl)-r-1-chlorocyclopropyl]-3-methylpenta-2,4-dienamide
(−)-(2E,4E)-N-Isobutyl-5-[(1R,2S)-c-(3,4-dichlorophenyl)-r1-chlorocyclopropyl]-3-methylpenta-2,4-dienamide
(−)-(2E,4E)-N-(S-1-Methylpropyl)-5-[(1R,2S)-c-(3,4-dichlorophenyl)-r-1-chlorocyclopropyl]-3-methylpenta-2,4-dienamide
(−)-(2E,4E)-N-(R-1-Methylpropyl)-5-[(1R,2S)-c-(3,4-dichlorophenyl)-r-1-)chlorocyclopropyl]-3-methylpenta-2,4-dienamide
(−)-(2E/Z,4E)-N-Isobutyl-5-[(1S,2R)-trans-2-(3,4-dibromophenyl)cyclopropyl]-3-methylpenta-2,4-dienamide
(+)-(2E/Z,4E)-N-Isobutyl-5-[(1R,2S)-trans-2-(3,4-dibromophenyl)cyclopropyl-3-methylpenta-2,4-dienamide By the term halo is meant fluoro, chloro, bromo and iodo. By the term hydrocarbyl group is meant, alkyl, alkenyl, alkynyl, aralkyl including a cyclic alkyl or alkenyl group optionally substituted by alkyl, alkenyl or alkynyl; and alkyl or alkenyl substituted by cyclic alkyl and alkenyl, and phenyl groups.

Salts of the compounds of the present invention will normally be acid addition salts. Such salts may be formed from mineral or organic or cycloalkyl acids. Preferred salts include those formed from hydrochloric, hydrobromic, sulphuric, citric, nitric, tartaric, phosphoric, lactic, benzoic, glutamic, aspartic, pyruvic, acetic, succinic, fumaric, maleic, oxaloacetic, hydroxynaphthoic, isethionic, stearic, methane-sulphonic, ethanesulphonic, benzenesulphonic, toluene-p-sulphonic, lactobionic, glucuronic, thiocyanic, propionic, embonic, naphthenoic and perchloric acids.

In a further aspect, the present invention provides a process for the preparation of a compound of the formula (II) as hereinbefore defined which comprises:

a) the reaction of the corresponding acid or acid derivative wherein the moiety $N_1HR^1$ is replaced by a group $Z^1$ with an amine $H_2NR^1$ wherein is as hereinbefore defined and $Z^1$ is hydroxy, $C_{1-6}$ alkoxy, halo or a phosphoroimidate ester (—P(O)(O-aryl)NH—aryl where aryl is $C_{6-10}$ aryl)

the formation of the $CR^2\!=\!CR^3CR^4\!=\!CR^5C(\!=\!O)NHR^1$ moiety through a Wittig type reaction.

and optionally thereafter converting one compound of the formula (I) into another compound of the formula (I) by methods well known to those skilled in the art.

Process (a) is normally carried out at a non-extreme temperature, for example between −25° and 150° C. in an anhydrous aprotic solvent, such as ether, dichloromethane, toluene or benzene. The precise conditions will be dependent on the nature of the group $Z^1$, for example when $Z^1$ is alkoxy the reaction is conveniently carried out at an elevated temperature, i.e. 50° to 125° C., and conveniently at reflux, preferably in the presence of a trialkylaluminium compound, such as trimethylaluminium, which forms a complex with the amine $H_2NR^1$. When $Z^1$ is halo or phosphoroimidate the reaction is conveniently carried out at 0° to 30° C. and suitably at room temperature preferably in the presence of a tertiary amine, such as triethylamine.

If the acid derivative is an acid halide, for example the acid chloride, then it may be formed from the corresponding acid by reaction with a suitable reagent such as oxalyl chloride or thionyl chloride. When $Z^1$ is a phosphoroimidate group then this is suitably formed from (PhO)P(—O)NHPhCl where Ph is phenyl. The acid, or the acid function in the compound $Q^2CR^2\!=\!CR^3CR^4\!=\!CR^5COZ^1$, may be prepared by hydrolysis of the corresponding ester wherein $Q^2$ represents the group.

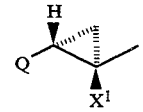

The esters may be prepared by a number of alternative routes, for example:
(i) conventional Wittig or Wadsworth-Emmons reaction, using for example an aldehyde and ethoxycarbonylmethylene triphenylphosphorane or an anion from triethylphosphonocrotonate or 3-methyl triethylphosphonocrotonate. This latter reaction may result in an isomeric mixture, for example a mixture of (Z) and (E) substituted dienoates; such a mixture may be reacted as above, and the resulting mixture of amides separated by chromatography or other convenient techniques. The Wittig-type reagent may be produced for example by the following route or a modification thereof:

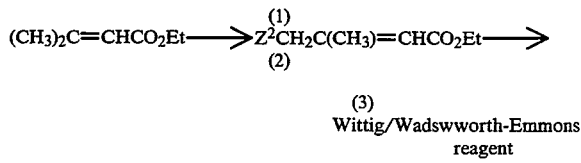

(1) $(CH_3)_2C=CHCO_2Et \longrightarrow Z^2CH_2C(CH_3)=CHCO_2Et \longrightarrow$
(2)
(3)
Wittig/Wadswworth-Emmons reagent wherein $Z^2=(aryl)_3P$, $(aryl)_2P(O)$ or $(C_{1-4}$ alkoxy$)_2P(O)$ where aryl is preferably phenyl and alkoxy is preferably ethoxy.

(1) N-bromo succinimide
(2) e.g. $(EtO)_3P$ or $(Ph)_3P$
(3) This reaction is normally carried out in the presence of a base such as lithium diisopropylamide, butyllithium, sodium alkoxide or sodium hydride.

(ii) by rearrangement and elimination of $HS(O)Z^3$ from a compound of formula:

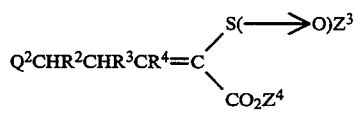

wherein $Q^2, R^2, R^3$ and $R^4$ are as hereinbefore defined, $Z^3$ is any suitable group, e.g. phenyl, substituted phenyl such as 4-chlorophenyl or $C_{1-4}$ alkyl, for example methyl, $Z^4$ is $C_{1-4}$ alkyl, e.g. methyl or ethyl.

The above compound may be obtained by reaction of a compound $QQ^1CHR^2CHR^3CR^4O$ with a compound $Z^3S(O)CH_2CO_2Z^4$.

(iii) By elimination a compound $Q^2CHR^2CR^3(OZ^5)CR^4=CR^5CO_2Z^4$ wherein $Q^2,R^2,R^3,R^4,R^5$ and $Z^4$ are as defined above, and $Z^5$ is hydrogen or $C_{1-4}$ acyl such as acetyl. The reaction is preferably carried out in an aromatic solvent, conveniently in the presence of a molybdenum catalyst and a base, such as bis-trimethylsilylacetamide.

The above compound may be obtained by the reaction of a suitable aldehyde with a suitable sulphenyl compound, followed by acylation.

(iv) reaction of a compound of formula $Q^2CR^2=CR^3C(=O)R^4$ with one of formula $Me_3SiCHR^5CO_2Z^4$, wherein $Q^2,R_2$ to $R^5$, $X^1$ and $Z^4$ are as hereinbefore defined.

This process may be carried out in an anhydrous solvent, e.g. tetrahydrofuran in the absence of oxygen, in the presence of a base, e.g. lithium cyclohexylisopropylamide.

(v) by reaction of a compound of formula $Q^2CR^2=CR^3C(OZ^6)=CR^5CO_2Z^4$ with a compound of formula $R^4M^1$ wherein $Q^2,X^1,R^2,R^3,R^4,R^5$ and $Z^4$ are as hereinbefore defined, $Z^6$ is a suitable group such as dialkylphosphate or trifluoromethanesulphonate and $M^1$ is a metal such as copper (I) or copper (I) associated with lithium or magnesium.

This process can be performed at low temperature in an anhydrous ethereal solvent such as diethyl ether, dimethyl sulphide or tetrahydrofuran in the absence of oxygen.

(vi) by reaction of a compound of formula $Q^2CR^2=CR^3M^2$ with one of formula $YCR^4=CR^5CO_2Z^4$, wherein $Q^2,X^1,R^2,R^3,R^4,R^5$ and $Z^4$ are as hereinbefore defined, Y is halo or tin and $M^2$ is a silyl or metal containing group, such as trimethylsilyl or a group containing zirconium, tin, aluminum or zinc, for example a bis(cyclopentadienyl) zirconium chloride group. This process is normally carried out at a non-extreme temperature i.e. between 0° and 100° C. and conveniently at room temperature, in a non-aqueous ethereal solvent such as tetrahydrofuran, in the presence of a palladium (O) catalyst, (such as bis (triphenylphosphine)palladium) and under an inert atmosphere of nitrogen or argon.

(vii) by elimination of $Z^3S(\rightarrow O)H$ from a compound of formula

$Q^2CR^2=CR^3CHR^4CR^5CO_2Z^4$
|
$S(\longrightarrow O)Z^3$ wherein $Q^2, X^1, R^2, R^3, R^4, R^5, Z^3$ and $Z^4$ are as hereinbefore defined.

The above compound may be obtained by reaction of a compound $QCHR^2CR^3=CHR^4$ with $Z^3S(O)CH_2CO_2Z^4$ Process (b) may be carried out by having an aldehyde or ketone group attached either to the amide/thioamide terminus or to the $QX^1$ fragment of formula (I) and then reacting this with the appropriate phosphorous ylid.
i.e.

$Q^2X^1(CR^2=CR^3)COR^4+Z^2CHR^5.C(=X)NHR^1$
or $Q^2X^1COR^2+Z^2CHR^3.CR^4=CR^5.C(=)NHR^1$
or
$Q^2X^1(CR^2=CR^3)CHR^5Z^2+R^5CO.C(=)NH.R^1$
wherein $Q^2, R^2, R^3, R^4, R^5, R^1, X^1$ and $Z^2$ are as hereinbefore defined.

Process (b) is carried out in an anhydrous inert solvent, for example an ether such as tetrahydrofuran, optionally in the presence of a base, and preferably in the absence of oxygen, e.g. under a nitrogen atmosphere, at a low temperature ($-60°$ to $20°$ C.). The phosphorous ylid may be obtained from its precursor as described above by reaction with a base such as lithium diisopropylamide, butyllithium, sodium alkoxide or sodium hydride. Compounds of the formula (I) wherein X is sulphur are preferably prepared by process (b) when $Z^2$ is a group $(C_{1-4}$ alkoxy$)_2P=O$. The aldehyde intermediates $Q^2CR^2=O$ may be prepared by acid hydrolysis of a ketal, enol ether or acetal in a solvent such as acetone-water or by oxidation of the appropriate alcohols using for example pyridinium chlorochromate, pyridinium dichromate or oxalyl chloride-dimethyl sulphoxide in a solvent such as dichloromethane. The aldehydes may also be prepared by reduction of the appropriate nitriles with a reagent such as diisobutylalumminium hydride in hexane.

The alcohols may be prepared by
a) reaction of $QCH=CX^2OH$ with $(Z^7)_2M^2$ and $CH_2X_2^3$ where $X^2$ is a group such as hydrogen, fluoro, chloro or methyl $X^3$ is a halogen such as iodine $Z^7$ is $C_{1-4}$ alkyl group such as ethyl and $M^2$ a metal such as zinc, in an inert solvent such as hexane or dichloromethane at moderate temperature ($-20°$ to $+20°$) and $CH_2$ and $CH=CX^2$ combine to form the cyclypropane ring, or b) reduction of an ester $Q^2CO_2Z^4$, or of the appropriate carboxylic acid with for instance diisobutylaluminium hydride or diborane in an inert solvent such as dichloromethane or tetrahydrofuran at moderate temperature ($-20°$ to $25°$). The esters may be prepared by reaction of a diazoacetate $N_2CH.CO_2Z^4$ with a compound $QCH{=}CH_2$ in the presence of a copper containing catalyst such as copper sulphate where CH and $CH{=}CH_2$ combine to form $Q^1$. The esters may also be prepared by the reaction of $QCH{=}CHCO_2Z^4$ with an anion derived from $Me_zS(O)_mC(Z^7)_2$ where $Z^7$ is hydrogen or $C_{1-6}$ alkyl and m is 1 or 2.

The resultant alcohol is separated into its enantiomers by the formation of a diastereomeric mixture by reaction with a suitable resolving agent, such as R-phenethylisocyanate when $X^1$ is fluoro, and camphorsulphonyl chloride when $X^1$ is chloro followed by fractional crystallisation to obtain the desired diastereoisomers and cleavage of the resolving agent, using sodium ethoxide in ethanol when $X^1$ is fluoro and sodium acetate in diglyme when $X^1$ is chloro.

When X is hydrogen, the enantiomeric aldehyde intermediate $QQ^1CHO$ may alternatively be prepared by assymetric induction of the trans cyclopropyl ring. This may be carried out by reaction of a compound of the formula (IV) wherein Q is as hereinbefore defined and $Pr^i$ is isopropyl.

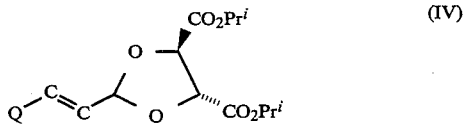
(IV)

with diiodomethane and diethylzinc in hexane to give the assymetric cyclopropane ring, viz a compound of formula (V), wherein Q and $Pr^i$ are as hereinbefore defined.

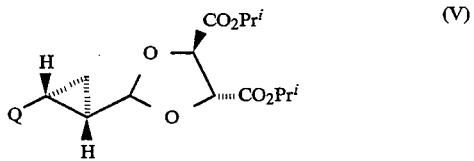
(V)

The dioxolane ring is then removed by acid hydrolysis, for example using dilute hydrochloric acid in tetrahydrofuran. The compound of the formula (IV) may be prepared as shown in Scheme.

The attached reaction scheme assists in illustrating the preparation of the intermediates and their conversion to compounds of formula (I). The intermediates of the present invention form a further aspect of the present invention and may be prepared where appropriate by standard methods other than those described.

The compounds of formula (I) may be used to control pests such as arthropods e.g. insect and acarine pests, and helminths, i.e. nematodes. Thus, the present invention provides a method for the control of arthropods and/or helminths which comprises administering to the arthropod and/or helminth or to their environment an arthropodically effective amount of a compound of the formula (I). The present invention also provides a method for the control and/or eradication of arthropod and/or helminth infestations of animals (including humans) and/or of plants,(including trees) and/or stored products which comprises administering to the animal or locus an effective amount of a compound of the formula (I). The present invention further provides for the compounds of the formula (I) for use in human and veterinary medicine, in public health control and in agriculture for the control of arthropod and/or helminth pests.

The compounds of formula (I) are of particular value in the protection of field, forage, plantation, glasshouse, orchard and vineyard crops, of ornamentals and of plantation and forest trees, for example, cereals (such as maize, wheat, rice, sorghum), cotton, tobacco, vegetables and salads (such as beans, cole crops, curcurbits, lettuce, onions, tomatoes and peppers), field crops (such as potato, sugar beet, ground nuts, soyabean, oil seed rape), sugar cane, grassland and forage (such as maize, sorghum, lucerne), plantations (such as of tea, coffee, cocoa, banana, oil palm, coconut, rubber, spices), orchards and groves (such as of stone and pip fruit, citrus, kiwifruit, avocado, mango, olives and walnuts), vineyards, ornamental plants, flowers and shrubs under glass and in gardens and parks, forest trees (both deciduous and evergreen) in forests, plantations and nurseries.

They are also valuable in the protection of timber (standing, felled, converted, stored or structural) from attack by sawflies (e.g. Urocerus) or beetles (e.g. scolytids, platypodids, lyctids, bostrychids, cerambycids, anobiids).

They have applications in the protection of stored products such as grains, fruits, nuts, spices and tobacco, whether whole, milled or compounded into products, from moth, beetle and mite attack. Also protected are stored animal products such as skins, hair, wool and feathers in natural or converted form (e.g. as carpets or textiles) from moth and beetle attack; also stored meat and fish from beetle, mite and fly attack.

The compounds of general formula (I) are of particular value in the control of arthropods or helminths which are injurious to, or spread or act as vectors of diseases in man and domestic animals, for example those hereinbefore mentioned, and more especially in the control of ticks, mites, lice, fleas, midges and biting, nuisance and myiasis flies.

The compounds of Formula (I) may be used for such purposes by application of the compounds themselves or in diluted form in known fashion as a dip, spray, fog, lacquer, foam, dust, powder, aqueous suspension, paste, gel, cream, shampoo, grease, combustible solid, vapourising mat, combustible coil, bait, dietary supplement, wettable powder, granule, aerosol, emulsifiable concentrate, oil suspensions, oil solutions, pressure-pack, impregnated article, pour on formulation or other standard formulations well known to those skilled in the art. Dip concentrates are not applied per se, but diluted with water and the animals immersed in a dipping bath containing the dip wash. Sprays may be applied by hand or by means of a spray race or arch. The animal, soil, plant or surface being treated may be saturated with the spray by means of high volume application or superficially coated with the spray by means of light or ultra low volume application. Aqueous suspensions may be applied in the same manner as sprays or dips. Dusts may be distributed by means of a powder applicator or, in the case of animals, incorporated in perforated bags attached to trees or rubbing bars. Pastes, shampoos and greases may be applied manually or distributed over the surface of an inert material, such as that against which animals rub and transfer the material to their skins. Pour-on formulations are dispensed as a unit of liquid of small volume on to the backs of animals such that all or most of the liquid is retained on the animals.

The compounds of Formula (I) may be prepared either as formulations ready for use on the animals, plants or surface or as formulations requiring dilution prior to application, but both types of formulation comprise a compound of Formula (I) in intimate admixture with one or more carriers or diluents. The carriers may be liquid, solid or gaseous or comprise mixtures of such substances, and the compound of Formula (I) may be present in a concentration of from 0.025 to 99% w/v depending upon whether the formulation requires further dilution.

Dusts, powders and granules and other solid formulations comprise the compound of Formula (I) in intimate admixture with a powdered solid inert carrier for example suitable clays, kaolin, bentonite, attapulgite, adsorbent carbon black, talc, mica, chalk, gypsum, tricalcium phosphate, powdered cork, magnesium siliate, vegetable carriers, starch and diatomaceous earths. Such solid formulations are generally prepared by impregnating the solid diluents with solutions of the compound of formula (I) in volatile solvents, evaporating the solvents and, if desired grinding the products so as to obtain powders and, if desired, granulating, compacting or encapsulating the products.

Sprays of a compound of Formula (I) may comprise a solution in an organic solvent (e.g. those listed below) or an emulsion in water (dip wash or spray wash) prepared in the field from an emulsifiable concentrate (otherwise known as a water miscible oil) which may also be used for dipping purposes. The concentrate preferably comprises a mixture of the active ingredient, with or without an organic solvent and one or more emulsifiers. Solvents may be present within wide limits but preferably in an amount of from 0 to 90% w/v of the composition and may be selected from kerosene, ketones, alcohols, xylene, aromatic naphtha, and other solvents known in the formulating art. The concentration of emulsifiers may be varied within wide limits but is preferably in the range of 5 to 25% w/v and the emulsifiers are conveniently non-ionic surface active agents including polyoxyalkylene esters of alkyl phenols and polyoxyethylene derivatives of hexitol anhydrides and anionic surface active agents including Na lauryl sulphate, fatty alcohol ether sulphates, Na and Ca salts of alkyl aryl sulphonates and alkyl sulphosuccinates. Cationic emulsifiers include benzalkonium chloride and quaternary ammonium ethosuphates.

Amphoteric emulsifiers include carboxymethylated oleic imidazoline and alkyl dimethyl betain.

Vaporising mats normally comprise cotton and cellulose mix compressed into a board of approximately 35×22×3 mm dimensions, treated with up to 0.3 ml of concentrate comprising the active ingredient in an organic solvent and optionally an antioxidant, dye and perfume. The insecticide is vaporised using a heat source such as an electrically operated mat heater.

Combustible solids normally comprise of wood powder and binder mixed with the active ingredient and formed into shaped (usually coiled) strips. Dye and fungicide may also be added. Wettable powders comprise an inert solid carrier, one or more surface active agents, and optionally stabilisers and/or anti-oxidants.

Emulsifiable concentrates comprise emulsifying agents, and often an organic solvent, such as kerosene, ketones, alcohols, xylenes, aromatic naphtha, and other solvents known in the art.

Wettable powders and emulsifiable concentrates will normally contain from 5 to 95% by weight of the active ingredient, and are diluted, for example with water, before use.

Lacquers comprise a solution of the active ingredient in an organic solvent, together with a resin, and optionally a plasticiser.

Dip washes may be prepared not only from emulsifiable concentrates but also from wettable powders, soap based dips and aqueous suspensions comprising a compound of Formula (I) in intimate admixture with a dispersing agent and one or more surface active agents.

Aqueous suspensions of a compound of Formula (I) may comprise a suspension in water together with suspending, stabilizing or other agents. The suspensions or solutions may be applied per se or in a diluted form in known fashion.

Greases (or ointments) may be prepared from vegetable oils, synthetic esters of fatty acids or wool fat together with an inert base such as soft paraffin. A compound of Formula (I) is preferably distributed uniformly through the mixture in solution or suspension. Greases may also be made from emulsifiable concentrates by diluting them with an ointment base.

Pastes and shampoos are also semi-solid preparations in which a compound of Formula (I) may be present as an uniform dispersion in a suitable base such as soft or liquid paraffin or made on a non-greasy basis with glycerin, mucilage or a suitable soap. As greases, shampoos and pastes are usually applied without further dilution they should contain the appropriate percentage of the compound of Formula (I) required for treatment.

Aerosol sprays may be prepared as a simple solution of the active ingredient in the aerosol propellant and co-solvent such as halogenated alkanes and the solvents referred to above, respectively. Pour-on formulations may be made as a solution or suspension of a compound of Formula (I) in a liquid medium. An avian or mammal host may also be protected against infestation of acarine ectoparasites by means of carrying a suitably-moulded, shaped plastics article impregnated with a compound of Formula (I). Such articles include impregnated collars, tags, bands, sheets and strips suitably attached to appropriate parts of the body. Suitably the plastics material is a polyvinyl chloride (PVC).

The concentration of the compound of Formula (I) to be applied to an animal, premises or outdoor areas will vary according to the compound chosen, the interval between treatments, the nature of the formulation and the likely infestation, but in general 0.001 to 20.0% w/v and preferably 0.01 to 10% of the compound should be present in the applied formulation. The amount of the compound deposited on an animal will vary according to the method of application, size of the animal, concentration of the compound in the applied formulation, factor by which the formulation is diluted and the nature of the formulation but in general will lie in the range of from 0.0001% to 0.5% w/w except for undiluted formulations such as pour-on formulations which in general will be deposited at a concentration in the range from 0.1 to 20.0% and preferably 0.1 to 10%. The amount of compound to be applied to stored products in general will lie in the range of from 0.1 to 20 ppm. Space sprays may be applied to give an average initial concentration of 0.001 to 1 mg of compound of formula (I) per cubic meter of treated space.

The compounds of formula (I) are also of use in the protection and treatment of plant species, in which case an effective insecticidal, acaricidal or nematocidal amount of the active ingredient is applied. The application rate will vary according to the compound chosen, the nature of the formulation, the mode of application, the plant species, the planting density and likely infestation and other like factors but in general, a suitable use rate for agricultural crops is in the range 0.001 to 3 kg/Ha and preferably between 0.01 and 1 kg/Ha. Typical formulations for agricultural use contain between 0.0001% and 50% of a compound of formula (I) and conveniently between 0.1 and 15% by weight of a compound of the formula (I).

Dusts, greases, pastes and aerosol formulations are usually applied in a random fashion as described above and concentrations of 0.001 to 20% w/v of a compound of Formula (I) in the applied formulation may be used.

The compounds of formula (I) have been found to have activity against the common housefly (*Musca domestica*). In addition, certain compounds of formula (I) have activity against other arthropod pests including *Myzus persicae, Tetranychus urticae. Plutella xylostella*, Culex spp. *Tribolium castaneum, Sitophilus granarius, Periplaneta ameircana* and *Blattella germanica*. The compounds of formula (I) are thus useful in the control of arthropods e.g. insects and acarines in any environment where these constitute pests, e.g. in agriculture, in animal husbandry, in public health control and in domestic situations.

Insect pests include members of the orders Coleoptera (e.g. Anobium, Ceutorhynchus, Rhynchophorus, Cosmopolites, Lissorhoptrus, Meligethes, Hypothenemus, Hylesinus, Acalymma, Lema, Psylliodes, Leptinotarsa, Gonocephalum, Agriotes, Dermolepida, Heteronychus, Phaedon, Tribolium, Sitophilus, Diabrotica, Anthonomus or Anthrenus spp.), Lepidoptera (e.g. Ephestia, Mamestra, Earias, Pectinophora, Ostrinia, Trichoplusia, Pieris, Laphygma, Agrotis, Amathes, Wiseana, Tryporysa, Diatraea, Sporganothis, Cydia, Archips, Plutella, Chilo, Heliothis, Spodoptera or Tineola spp.), Diptera (e.g. Musca, Aedes, Anopheles, Culex, Glossina, Simulium, Stomoxys, Haematobia, Tabanus, Hydrotaea, Lucilia, Chrysomia, Callitroga, Dermatobia, Gasterophilus, Hypoderma, Hylemyia, Atherigona, Chlorops, Phytomyza, Ceratitis, Liriomyza and Melophagus spp.), Phthiraptera (Malophaga e.g. Damalina spp. and Anoplura e.g. Linognathus and Haematopinus spp.), Hemiptera (e.g. Aphis, Bemisia, Phorodon, Aeneolamia, Empoasca, Parkinsiella, Pyrilla, Aonidiella, Coccus, Pseudococus, Helopeltis, Lygus, Dysdercus, Oxycarenus, Nezara, Aleurodes, Triatoma, Psylla, Mysus, Megoura, Phylloxera, Adelyes, Niloparvata, Nephrotetix or Cimex spp.), Orthoptera (e.g. Locusta, Gryllus, Schistocerca or Acheta spp.), Dictyoptera (e.g. Blattella, Periplaneta or Blatta spp.), Hymenoptera (e.g. Athalia, Cephus, Atta, Solenopsis or Monomorium spp.), Isoptera (e.g. Odontotermes and Reticulitermes spp.), Siphonaptera (e.g. Ctenocephalides or Pulex spp.), Thysanura (e.g. Lepisma spp.), Dermaptera (e.g. Forficula spp.), Pscoptera (e.g. Peripsocus spp.) and Thysanoptera (e.g. *Thrips tabaci*),.

Acarine pests include ticks, e.g. members of the genera Boophilus, Ornithodorus, Rhipicephalus, Amblyomma, Hyalomma, Ixodes, Haemaphysalis, Dermacentor and Anocentor, and mites and manges such as Acarus, Tetranychus, Psoroptes, Notoednes, Sarcoptes, Psorergates, Chorioptes, Eutrombicula, Demodex, Panonychus, Bryobia, Eriophyes, Blaniulus, Polyphagotarsonemus, Scutigerella, and Oniscus spp.

Nematodes which attack plants and trees of importance to agriculture, forestry, horticulture either directly or by spreading bacterial, viral, mycoplasma or, fungal diseases of the plants, include root-knot nematodes such as Meloidogyne spp. (e.g. *M. incognita*); cyst nematodes such as Globodera spp. (e.g. *G. rostochiensis*); Heterodera spp. (e.g. hydrogen. *avenae*); Radopholus spp. (e.g.*R. similis*); lesion nematodes such as Pratvlenchus spp. (e.g. *P. pratensts*); Belonolaimus spp. (e.g. *B. gracilis*); Tylenchulus spp. (e.g. *T. semipenetrans*); Rotylenchulus spp. (e.g. *R. reinformis*); Rotylenchus spp. (e.g. *R. robustus*); Helicotylenchus spp. (e.g. hydrogen. *multicinctus*); Hemicycliophora spp. (e.g. hydrogen. *gracilis*); Criconemoides spp. (e.g. *C. similis*); Trichodorus spp. (e.g. *T primitivus*); dagger nematodes such as Xiphinema spp. (e.g. *X. diverstcaudatum*), Longidorus spp (e.g. *L. elongatus*); Hoplolaimus spp. (e.g. hydrogen. *coronatus*); Aphelenchoides spp. (e.g. *A. ritzema-bosi, A. besseyi*); stem and bulb eelworms such as Ditylenchus spp. (e.g. *D. dipsaci*).

Compounds of the invention may be combined with one or more other pesticidally active ingredients (for example pyrethroids, carbamates and organophosphates) and/or with attractants, repellents, bacteriocides, fungicides, nematocides, anthelmintics and the like. Furthermore, it has been found that the activity of the compounds of the invention may be enhanced by the addition of a synergist or potentiator, for example: one of the oxidase inhibitor class of synergists, such as piperonyl butoxide or propyl 2-propynylphenylphosphonate; a second compound of the invention; or a pyrethroid pesticidal compound. When an oxidase inhibitor synergist is present in a formula of the invention, the ratio of synergist to compound of Formula (I) will be in the range 25:1–1:25 e.g. about 10:1.

Stabilisers for preventing any chemical degradation which may occur with the compounds of the invention include, for example, antioxidants (such as tocopherols, butylhydroxyanisole and butylhydroxytoluene) and scavengers (such as epichlorhydrin) and organic or inorganic bases e.g. trialkylamines such as triethylamine which can act as basic stabilises and as scavengers.

Industrial Applicability

Compounds of the present invention show activity as pesticides.

The following examples illustrate, in a non-limiting manner, preferred aspects of the invention.

| Formulations | |
|---|---|
| 1. Emulsifiable Concentrate | |
| Compound of formula (1) | 10.00 |
| Alkyl phenol ethoxylate* | 7.50 |
| Alkyl aryl sulphonate* | 2.50 |
| $C_{8-13}$ aromatic solvent | 80.00 |
| | 100.00 |
| 2. Emulsifiable Concentrate | |
| Compound of formula (I) | 10.00 |
| Alkyl phenol ethoxylate* | 2.50 |
| Alkyl aryl sulphonate* | 2.50 |
| Ketonic solvent | 64.00 |
| $C_{8-13}$ aromatic solvent | 18.00 |
| Antioxidant | 3.00 |
| | 100.00 |
| 3. Wettable Powder | |
| Compound of formula (I) | 5.00 |
| $C_{8-13}$ aromatic solvent | 7.00 |
| $C_{18}$ *aromatic solvent* | 28.00 |
| China clay | 10.00 |

| Formulations | |
|---|---|
| Alkyl aryl sulphonate* | 1.00 |
| Napthalene sulphonic acid* | 3.00 |
| Diatomaceous earth | 46.00 |
| | 100.00 |
| 4. Dust | |
| Compound of formula (I) | 0.50 |
| Talc | 99.50 |
| | 100.00 |
| 5. Bait | |
| Compound of formula (I) | 0.5 |
| Sugar | 79.5 |
| Paraffin wax | 20.0 |
| | 100.00 |
| 6. Emulsion Concentrate | |
| Compound of formula (I) | 5.00 |
| $C_{8-13}$ aromatic solvent | 32.00 |
| Cetyl alcohol | 3.00 |
| Polyoxyethylene glycerol monooleate* | 0.75 |
| Polyoxyethylene sorbitan esters* | 0.25 |
| Silicone solution | 0.1 |
| Water | 58.9 |
| | 100.00 |
| 7. Suspension Concentrate | |
| Compound of formula (I) | 10.00 |
| Alkyl aryl ethoxylate* | 3.00 |
| Silicone solution | 0.1 |
| Alkane diol | 5.0 |
| Fumed silica | 0.50 |
| Xanthan gum | 0.20 |
| Water | 80.0 |
| Buffering agent | 1.2 |
| | 100.00 |
| 8. Microemulsion | |
| Compound of formula (I) | 10.00 |
| Polyoxyethylene glycerol monooleate* | 10.00 |
| Alkane diol | 4.00 |
| Water | 76.00 |
| | 100.00 |
| 9. Water Dispersible Granules | |
| Compound of formula (I) | 70.00 |
| Polyvinyl pyrrolidine | 2.50 |
| Alkyl aryl ethoxylate | 1.25 |
| Alkyl aryl sulphonate | 1.25 |
| China clay | 25.00 |
| | 100.00 |
| 10. Granules | |
| Compound of formula (I) | 2.00 |
| Alkyl phenol ethoxylate* | 5.00 |
| Alkyl aryl sulphonate* | 3.00 |
| $C_{8-13}$ aromatic solvent | 20.00 |
| Kieselguhr granules | 70.00 |
| | 100.00 |
| 11. Aerosol (pressure pack) | |
| Compound of formula (I) | 0.3 |
| Piperonyl butoxide | 1.5 |
| $C_{8-13}$ saturated hydrocarbon solvent | 58.2 |
| Butane | 40.0 |
| | 100.00 |
| 12. Aerosol (pressure pack) | |
| Compound of formula (I) | 0.3 |
| $C_{8-13}$ saturated hydrocarbon solvent | 10.0 |
| Sorbitan monooleate* | 1.0 |
| Water | 40.0 |
| Butane | 48.7 |
| | 100.00 |
| 13. Aerosol (pressure pack) | |
| Compound of formula (I) | 1.00 |
| $CO_2$ | 3.00 |
| Polyoxyethylene glycerol monooleate* | 1.40 |
| Propanone | 38.00 |
| Water | 56.60 |
| | 100.00 |
| 14. Lacquer | |
| Compound of formula (I) | 2.50 |
| Resin | 5.00 |

| Formulations | |
|---|---|
| Antioxidant | 0.50 |
| High aromatic white spirit | 92.0 |
| | 100.00 |
| 15. Spray (ready to use) | |
| Compound of formula (I) | 0.10 |
| Antioxidant | 0.10 |
| Odourless kerosene | 99.8 |
| | 100.00 |
| 16. Poteniated Spray (ready to use) | |
| Compound of formula (1) | 0.10 |
| Piperonyl butoxide | 0.50 |
| Antioxidant | 0.10 |
| Odourless kerosene | 99.30 |
| | 100.00 |
| 17. Microencapsulated | |
| Compound of formula (I) | 10.0 |
| $C_{8-13}$ aromatic solvent | 10.0 |
| Aromatic di-isocyanate# | 4.5 |
| Alkyl phenol ethoxylate* | 6.0 |
| Alkyl diamine# | 1.0 |
| Diethylene triamine | 1.0 |
| Concentrated hydrochloric acid | 2.2 |
| Xanthan gum | 0.2 |
| Fumed silica | 0.5 |
| Water | 64.6 |
| | 100.00 |

\* = Surfactant
# = react to form the polyurea walls of the microcapsule
Antioxidant could be any of the following individually or combined
Butylated hydroxytoluene
Butylated hydroxyanisole
Vitamin C (ascorbic acid)

The following Examples illustrate, in a non-limiting manner, preferred aspects of the invention.

EXPERIMENTAL

General Synthetic Methods and Procedures

Various compounds were synthesised and characterised in accordance with the following experimental procedures.

$^1$H N.m.r. spectra were obtained on a Bruker AM-250 spectrometer in deuterochloroform solutions with tetramethylsilane as internal standard and are expressed as ppm from TMS, number of protons, number of peaks, coupling constant J Hz.

Progress of reactions could also be conveniently monitored on Aluminium sheets (40×80 mm) precoated with 0.25 mm layers of silica gel with fluorescent indicator and developed in appropriate solvent or solvent mixture. Temperatures are in degrees Celsius throughout.

Conventional work up was performed as follows:

The reaction mixture was partitioned between an organic solvent and water. The phases were separated and the organic phase washed with at least an equivalent volume of dilute aqueous base as appropriate, and then with a saturated brine wash. The organic phase was then dried over a drying agent, suitably magnesium sulphate, and filtered. The volatile solvents were removed and the resulting product subjected to the appropriate purification and used in the next stage of synthesis or analysed as the final product.

The aldehyde, cinnamic acid and amine starting materials were obtained from Aldrich, BDH, Fluorochem, Fluka or Lancaster Synthesis with the exception of the following whose preparation is described below.

EXAMPLE 1

(−)-(2E,4E)-N-(2-Methylprop-2-enyl)-5-[(1R,2S)-c-2-(3,4-dibromophenyl)-r-1-fluorocyclopropyl]3-methylpenta-2,4-dieneamide (Compound 1).

(±)-c-2-(3,4-Dibromophenyl)-r-1-fluorocyclopropylmethanol (11 g) and (+)-(R)-α-methylbenzylisocyanate (5 g) were stirred at 80° C. for 60 hours under nitrogen. The resulting crude product was subjected to chromatography on silica followed by fractional crystallisation to give [(1R,2R)-c-2-(3,4-dibromophenyl)-r-1-fluorocyclopropylmethyl]-(αR)-α-methylbenzyl carbamate (2.0 g, m.pt. 94.3° C.) and [(1S,2S)-c-1-fluoro-r-2-(3,4-dibromophenyl)cyclopropylmethyl]-(αR)-α-methylbenzyl carbamate (3.0 g, m.pt. 118.6° C.) in addition to 6.25 g of the mixture. Absolute stereochemistries were confirmed by X-ray.

[(1S,2S)-c-2-(3,4-Dibromophenyl)-r-1-fluorocyclopropylmethyl]-(αR)-α-methylbenzyl carbamate (3.7 g) was added to a solution of sodium ethoxide (ex Aldrich) (0.11 g) in ethanol (2 ml) under nitrogen and the mixture was heated to 70° C. for 30 minutes. The mixture was cooled and concentrated in vacuo. Chromatography on silica gave (−)-(1S,2S)-c-2-(3,4-dibromophenyl)-r-1-fluorocyclopropylmethanol 2.42 g, m.pt. 82° C., $[α_D]−28.9°$, c. 1.00 (EtOH)).

Oxalyl chloride (ex Aldrich) (0.72 ml) was dissolved in dichloromethane (10 ml) and cooled to −70° C. under nitrogen. Dimethyl sulphoxide (1.17 ml) (ex BDH) in dichloromethane (1 ml) was added dropwise. After 5 minutes the above alcohol (2.42 g) in dichloromethane (5 ml) was added and the suspension stirred at −70° C. for thirty minutes. Triethylamine (ex Aldrich) (5.2 ml) was added and the mixture allowed to warm to 0° C. over one hour. Work up in the conventional manner gave (−)-(1S,2S)-c-2-(3,4-dibromophenyl)-r-1-fluorocyclopropylmethanal (2.4 g, $[α_D]−69.7°$ (c 1.00, EtOH)).

A solution of lithium diisopropylamide in dry tetrahydrofuran prepared from n-butyl lithium (ex Aldrich) (4.7 ml) and diisopropylamine (ex Aldrich) (1.1 ml) was treated at −60° C. with triethyl 3-methylphosphonocrotonate (1.97 g) in tetrahydrofuran under nitrogen. After 2 hours at −60° C. the above aldehyde (2.4 g) was added. After 18 hours at 25° C. the mixture was partitioned between ether and water and the ethereal fraction worked up as above. Purification by chromatography on silica (ether/hexane) gave (−)-(2E/Z,4E)-Ethyl-5-[(1R,2S)-c-2-(3,4-dibromophenyl)-r-1-fluorocyclopropyl]-3-methylpenta-2,4-dienoate, (2.82 g, 2E:2Z 3:2. $[α]_D−136°$ (c. 1.00, EtOH)).

To the above ester (2.76 g) in ethanol (100 ml) was added a solution of potassium hydroxide (ex BDH) (1.25 g) in water (25 ml). After 18 hours at room temperature the solution was concentrated in vacuo. The carboxylic acid salt residue was dissolved in a small amount of water and acidified with concentrated hydrochloric acid. Ether extraction, drying over magnesium sulphate and concentration in vacuo gave (−)-(2E/Z,4E)-5-[(1S,2R)-c-2-(3,4-dibromophenyl)-r-1-fluorocyclopropyl]-3-methyl penta-2,4-dienoic acid (2.45 g, $[α]_D−2.45$ g (c. 1.00, EtOH).

To a stirred suspension of the above acid (2.4 g) in dichloromethane (60 ml) under nitrogen at 0° C. was added oxalyl chloride (0.63 ml) followed by one drop of dimethylformamide. After 2 hours at room temperature the solvent was removed in vacuo. The residue was suspended in ether (60 ml) and cooled to 0° C., triethylamine (1.0 ml) and 2-methyl prop-2-enylamine (0.65 ml, ex Aldrich) were added and the mixture stirred for 18 hours at room temperature. Water was added and the mixture was worked up in a conventional manner. Chromatography on silica (ether/hexane) gave the title compound (0.6 g, m.pt. 125° C., $[α]_D −171°$ (c. 1.00, EtOH)).

Also isolated was (−)-(2E/Z,4E)-N-(2-Methylprop-2-enyl)-5-[(1R,2S)-c-2-(3.4-dibromophenyl)-r-1-fluorocyclopropyl]-3-methylpenta-2,4-dienamide, (Compound 2) (1.4 g, 2E:4E 3:2. $[α]_D−132°$ (c. 1.00, EtOH)).

Using the same experimental methods, [(1R,2R,)-c-2-(3,4-dibromophenyl-r-1-fluorocyclopropylmethyl]-(αR)-a-methylbenzyl carbamate was converted into (+)-(2E,4E)-N-(2-Methylprop-2-enyl)-5-[(1S,2R)-c-(3,-4--dibromophenyl)-r-1-fluorocyclopropyl]-3-methylpenta-2,4-dienamide, (Compound 3) (0.11 g, $[α_D]+170°$ (c 1.00 EtOH)) and (+)-(2E/Z,4E)-N-(2-Methylprop-2-enyl)-5-[(1S,2R)-c-2-(3,4-dibromophenyl)-r-fluorocyclopropyl]-3-methylpenta-2,4-dieneamide, (Compound 4) (0.78 g, 2E:2Z 5:4. $[α_D]+131°$ (c 1.00 EtOH)).

EXAMPLE 2

(+)-(2E,4E)-N-Isobutyl-5-[(1S,2R)-c-2-(3,4-dichlorophenyl)-r-1-chlorocyclopropyl]-3-methylpenta-2,4-dienamide, (Compound 5).

(±)-c-2-(3,4-Dichlorophenyl)-r-1-chlorocyclopropylmethanol (8.0 g) in dichloromethane (160 ml) under nitrogen at −20° C. was treated successively with triethylamine (5.3 ml) and (−)-(1S)-10-Camphorsulphonyl chloride (8.78 g, ex Aldrich). After 18 hours at −5° C. the mixture was poured into water and worked up in a conventional manner to give [(1S,2S)-(−)-c-2-(3.4-dichlorophenyl)-r-1-chlorocyclopropylmethyl]-(1-S)-10-camphor sulphonate (4.8 g, $[α_D]−11.3°$ (c 1.00, CHCl3)) and [(1R,2R)-(+)-c-2-(3,4-dichlorophenyl)-r-1-chlorocyclopropylmethyl]-(1-S)-10-camphor sulphonate (4.7 g, $[α_D]+11.3°$ (c 1.00, CHCl3)). Also isolated were 2.7 g of the diastereoisomeric mixture. Absolute stereochemistries were determined by X-ray crystallography.

To a stirred suspension of (+)-[(1R,2R)-c-2-(3,4-dichlorophenyl)-r-1-chlorocyclopropylmethyl]-(1S)-10-camphor sulphonate (2.66 g) in 2-methoxyethanol (5 ml) (ex Aldrich) was added sodium acetate (2 g) (ex Aldrich) and the mixture heated to reflux for 7 hours. The mixture was cooled, diluted with water and extracted with ether. Conventional work up and chromatography (silica, ether/hexane) gave (+)-(1R,2R)-c-2-(3,4-dichlorophenyl)-r-1cyclopropylmethanol as a colourless oil (0.5 g, $[α_D]+28°$, c. 1.00 (EtOH)).

Oxalyl chloride (0.19 ml) was dissolved in dichloromethane (3 ml) and cooled to −70° C. under nitrogen. Dimethyl sulphoxide (0.31 ml) in Dichloromethane (1 ml) was added dropwise. After 5 minutes the above alcohol (0.5 g) in dichloromethane (1 ml) was added and the suspension stirred at −70° C. for thirty minutes. Triethylamine (1.38 ml) was added and the mixture allowed to warm to 0° C. over one hour. Work up in the conventional manner gave (+)-(1R,2RS)-c-2-(3,4-dichlorophenyl)-r-1-chlorocyclopropylmethanal (0.49 g).

A solution of lithium diisopropylamide in dry tetrahydrofuran prepared from n-butyl lithium (1.24 ml) and diisopropylamide (0.28 ml) was treated at −60° C. with triethyl 3-methylphosphonocrotonate (0.52 g) in tetrahydrofuran under nitrogen. After 2 hours at −60° C. the above aldehyde (0.49 g) was added. After 18 hours at 25° C. the mixture was partitioned between ether and water and the ethereal fraction worked up as above. Purification by chromatography on silica (ether/hexane) gave (+)-(2E/Z,4E)-ethyl-5-[(1S,2R)-c-2-(3,4-dichlorophenyl)-r-1-chlorocyclopropyl]-3-methylpenta-2,4-dienoate, (0.7 g, 2E:2Z, 7:3).

To the above ester (0.7 g) in ethanol (10 ml) was added a solution of potassium hydroxide (0.38 g) in water (2.5 ml). After 18 hours at room temperature the solution was concentrated in vacuo. The carboxylic acid salt residue was dissolved in a small amount of water and acidified with concentrated hydrochloric acid. Ether extraction, drying over magnesium sulphate and concentration in vacuo gave (+)-(2E/Z,4E)-5-[(1R,2S)-c-2-(3,4-dichlorophenyl)-r-1-chlorocyclopropyl]-3-methylpenta-2,4-dienoic acid.

To the above acid (0.58 g) in dichloromethane (5 ml) at 25° C. under nitrogen was added triethylamine (0.49 ml), N-phenylphosphoramidochloridate (ex Aldrich) (0.47 g) and isobutylamine (ex Aldrich, O.17 ml) successively. After 18 hours at room temperature, the mixture was subjected to a conventional work up to give, after chromatography (silica, ether/hexane), the title compound (0.23 g, m.pt. 114° C., $[\alpha_D]+164°$ (c. 1.00, EtOH)).

By a procedure identical to that described above, (−)-(2E,4E)-N-Isobutyl-5-[(1R,2S)-c-2-(3,4-dichlorophenyl)-r-1-chlorocyclopropyl]-3-methylpenta-2,4-dieneamide, (Compound 6) was prepared from (−)-[(1S,2S)-c-2-(3,4-dichlorophenyl)-r-1-chlorocyclopropylmethyl]-(1S)-1O-camphorsulphonate (0.3 g, m.pt. 114° C., $[\alpha_D]-164°$ (c 1.00, EtOH).

Using the same experimental methods, the following compounds were prepared from (−)-(2E/Z,4E)-5-[(1R,2S)-c-2-(3,4-dichlorophenyl)-r-1chlorocyclopropyl]-3-methylpenta-2,4-dienoic acid using (S)-(+)-sec-butylamine and (R)-(−)-sec-butylamine (ex Aldrich) in place of isobutylamine.

(−)-(2E,4E)-N-(S-1-Methylpropyl)-5-[(1R,2S)-c-2-(3,4-dichlorophenyl)-r-1-chlorocyclopropyl]-3-methylpenta- 2,4-dieneamide, (Compound 7). (0.146 g, $[\alpha_D]-141°$ (c 1.00, EtOH)).

(−)-(2E,4E)-N-(R-1-Methylpropyl)-5-[(1R,2S)-c-2-(3,4-dichlorophenyl)-r-1-chlorocyclopropyl]-3-methylpenta-2,4-dieneamide, (Compound 8). (0.119 g, $[\alpha_D]-186°$ (c 1.00, EtOH)).

EXAMPLE 3

(−)-(2E,4E)-N-Isobutyl-5-[(1S,2R)-trans-2-(3,4-dibromophenyl)cyclopropyl]-3-methylpenta-2,4-dieneamide, (Compound 9).

The title compound was prepared by a procedure analogous to that used in EP 369 762, example 12, compound 56. 3,4-Dibromobenzaldehyde and triethyl 3-methylphosphonocrotonate were used in place of 3,4-dibromobenzaldehyde and triethyl phosphonocrotonate (0.324 g, $[\alpha_D]-188°$ (c 0.99, EtOH)).

(+)-(2E,4E)-N-Isobutyl-5-[(1R,2S)-trans-2-(3,4-dibromophenyl)cyclopropyl]-3-methylpenta-2,4-dieneamide (Compound 10), was prepared in an analogous fashion using D-(−)-diisopropyltartrate in place of L-(+)-diisopropyl-tartrate (0.23 g, $[\alpha_D]+154°$ (c 0.94, EtOH)).

NMR Data

Compound 1. 7.58(2H,m), 7.04(1H,dd), 6.38(1H,d), 5.84(1H,dd), 5.73(1H,s), 5.59(1H,m), 4.82(2H,s), 3.90(2H,d), 2.31(3H,d), 2.29(1H,m), 1.78(1H,m), 1.76(3H,s), 1.55(1H,m).

2. 7.85 & 6.39(1H,d), 7.58(2H,m), 7.08(1H,dd), 6.11 & 5.83(1H,dd), 5.77 & 5.68(1H,d), 5.60(1H,m), 4.88(2H,s), 3.89(2H,m), 2.30 & 2.00(3H,d), 2.25(1H,m), 1.70(1H,m), 1.76(3H,s), 1.55(1H,m).

3. 7.58(2H,m), 7.05(1H,dd), 6.39(1H,d), 5.86(1H,dd), 5.73(1H,s), 5.58(1H,m), 4.85(2H,s), 3.90(2H,d), 2.31(3H,d), 2.28(1H,m), 1.78(1H,m), 1.76(3H,s), 1.55(1H,m).

4. 7.85 & 6.39(1H,d), 7.58(2H,m), 7.08(1H,dd), 6.11 & 5.83(1H,dd), 5.77 & 5.68(1H,d), 5.60(1H,m), 4.88(2H,s), 3.89(2H,m), 2.30 & 2.00(3H,d), 2.25(1H,m), 1.70(1H,m), 1.76(3H,s), 1.55(1H,m).

5. 7.40(1H,d), 7.32(1H,d), 7.09(1H,d), 6.43(1H,d), 5.92(1H,d), 5.77(1H,s), 5.55(1H,m), 3.14(2H,t), 2.48(1H,dd), 2.30(3H,d), 1.77(3H,m), 0.93(6H,d).

6. 7.40(1H,d), 7.32(1H,d), 7.09(1H, dd ), 6.43(1H,d), 5.92(1H,d), 5.77(1H,s), 5.55(1H,m), 3.14(2H,t), 2.48(1H,dd), 2.30(3H,d), 1.77(3H,m), 0.93(6H,d).

7. 7.40(1H,d), 7.31(1H,d), 7.08(1H,dd), 6.41(1H,d), 5.92(1H,d), 5.70(1H,s), 5.26(1H,d$_{broad}$), 4.00(1H,m), 2.47(1H,dd), 2.29(3H,d), 1.72(2H,m), 1.42(2H,m) 1.13(3H,d), 0.92(3H,t).

8. 7.40(1H,d), 7.31(1H,d), 7.08(1H,dd), 6.41(1H,d), 5.92(1H,d), 5.70(1H,s), 5.26(1H,d$_{broad}$), 4.00(1H,m), 2.47(1H,dd), 2.29(3H,d), 1.72(2H,m), 1.42(2H,m) 1.13(3H,d), 0.92(3H,t).

9. 7.49(1H,d), 7.33(1H,d), 6.88(1H,dd), 6.15(1H,d), 5.71(1H,m), 5.63(1H,dd), 5.61(1H,s), 3.12(2H,t), 2.23(3H,s), 1.95(1H,m), 1.75(2H,m), 1.26(2H,m). 0.91(6H,d).

10. 7.49(1H,d), 7.33(1H,d), 6.88(1H,dd), 6.15(1H,d), 5.71(1H,m), 5.63(1H,dd), 5.61(1H,s), 3.12(2H,t), 2.23(3H,s), 1.95(1H,m), 1.75(2H,m), 1.26(2H,m). 0.91(6H,d).

BIOLOGICAL DATA

The following examples illustrate, in a non-limiting manner, the pesticidal activity of compounds of formula (I):

EXAMPLE A—SPRAY TESTS

The activity of compounds of the invention were tested by dissolving the compounds in acetone (5%) and then diluting in water: "Synperonic" (94.5%:0.5%) to give a water emulsion. The solution was then used to treat the following insects, for which activity was observed at the following spray rates:

*Spodoptera littoralis*

Uninfested leaves were sprayed with the test solution containing the compound and left to dry. These were then infested with 10 newly hatched larvae. Mortality was assessed after 3 days.

The following compounds were active at 250 ppm or less:
3, 4, 6, 5, 9, 10, 7 and 8.

The following compounds were active at 50 ppm or less:
1,2.

EXAMPLE B—TOPICAL APPLICATION TESTS

Blattella germanica 0.5μl of a solution of the compound in butanone (with or without piperonyl butoxide) was topically applied to male *B. germanica*. Mortality was assessed after 6 days.

The following compounds were active at 10μg or less (+10μg piperonyl butoxide):
6, 7, 8, 9 and 10.

Topical application to housefly (*Musca domestica*)

The compounds were administered topically to female *Musca domestica* in butanone solution, either alone or in conjunction with a synergist (6μg piperonyl butoxide). The flies were kept with sugar water and the mortality were assessed after 48 hours.

The following compounds were active at 1μg or less (+6μg piperonyl butoxide)
3, 4, 7 and 8.

The following compounds were active at 0.2μg or less (+6μg piperonyl butoxide):
1, 2, 6, 9 and 10.

We claim:

1. A compound of the formula:
$Q^2CR^2\!\!=\!\!CR^3CR^4\!\!=\!\!CR^5\!\!-\!\!C(\!=\!O)Z^1$
$Q^2(CR^2\!\!=\!\!CR^3)COR^4$ or
$Q^2(CR^2\!\!=\!\!CR^3)CR^5Z^2$
or a salt thereof wherein $Q^2$ represents

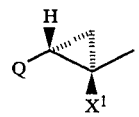

Q is a monocyclic aromatic ring or a fused bicyclic ring system of which at least one ring is aromatic containing 9 or 10 atoms of which one may be nitrogen and the rest carbon, each ring system being optionally substituted, or Q is a dihalovinyl group or a group $R^6\!\!-\!\!C\!\!\equiv\!\!C\!\!-\!\!$where $R^6$ is $C_{1\text{-}4}$ alkyl, tri $C_{1\text{-}4}$ alkylsilyl, halogen or hydrogen;

$X^1$ is hydrogen, fluoro or chloro;

$R^2$, $R^3$, $R^4$ and $R^5$ are the same or different with at least one being hydrogen and the others being independently selected from hydrogen, halo, $C_{1\text{-}4}$ alkyl or $C_{1\text{-}4}$ haloalkyl;

$Z^1$ is hydroxy, $C_{1\text{-}6}$ alkoxy, halo or a phosphoroimidate ester $-\!\!P(O)(O\text{-aryl})NH\text{-aryl}$ where aryl is $C_{6\text{-}10}$ aryl; and $Z^2$ is $(aryl)_3$ P, $(aryl)_2P(O)$ or $(C_{1\text{-}4}\text{ alkoxy})_2P(O)$ where alkoxy is $C_{1\text{-}4}$ alkoxy and aryl is $C_{6\text{-}10}$.

* * * * *